US007160683B2

(12) United States Patent
Ohtani et al.

(10) Patent No.: US 7,160,683 B2
(45) Date of Patent: Jan. 9, 2007

(54) METHOD OF TESTING FOR BRONCHIAL ASTHMA

(75) Inventors: Noriko Ohtani, Kawasaki (JP); Keiko Matsui, Kawasaki (JP); Nei Yoshida, Kawasaki (JP); Yuji Sugita, Kawasaki (JP); Yuhei Hamasaki, Saga (JP); Kenji Izuhara, Saga (JP)

(73) Assignee: Genox Research, Inc., Ibaraki (JP)

( * ) Notice: Subject to any disclaimer, the term of this patent is extended or adjusted under 35 U.S.C. 154(b) by 198 days.

(21) Appl. No.: 10/214,793

(22) Filed: Aug. 7, 2002

(65) Prior Publication Data

US 2003/0099979 A1 May 29, 2003

(30) Foreign Application Priority Data

Aug. 7, 2001 (JP) ............................. 2001-239857

(51) Int. Cl.
*C12Q 1/00* (2006.01)
*C12Q 1/68* (2006.01)
*G01N 33/53* (2006.01)
*G01N 33/68* (2006.01)

(52) U.S. Cl. ............................. 435/6; 4/7.1; 4/23; 4/24; 4/91.2; 436/86

(58) Field of Classification Search ................. 435/7.1, 435/4, 6, 23, 24, 91.2; 436/86
See application file for complete search history.

(56) References Cited

U.S. PATENT DOCUMENTS

2003/0099979 A1* 5/2003 Ohtani et al. ................... 435/6

OTHER PUBLICATIONS

Cheah et al., J Clinical Pathology, vol. 47, pp. 535-537, 1994.*
Akimoto et al., "Abrogation of bronchial eosinophilic inflammation and airway hyperreactivity in signal transducers and activators of transcription (STAT)6-deficient mice," J. Exp. Med., 187:1537-1542 [1998].
Berger and Kimmel, "Guide to Molecular Cloning Techniques," Method in Enzymology, Academic Press Inc., Orlando, FL [1987] title and copyright pages.
Borish et al., "Interleukin-4 receptor in moderate atopic asthma," Am. J. Respir. Crit. Care Med., 160:912-922 [1999].
Cataltepe et al., "Development of specific monoclonal antibodies and a sensitive discriminatory immunoassay for the circulating tumor markers SCCA1 and SCCA2," Clin. Chim. Acta, 295:107-127 [2000].
Gibson et al., "A novel method for real time quantitative RT-PCR," Genome Research, 6:995-1001 [1996].
Grunig et al., "Requirement for IL-13 Independently of IL-4 in experimental asthma," Science, 282:2261-2263 [1998].
Hames and Higgins, *Genes Probes: A Practical Approach*, IRL Press, Oxford [1985] title and copyright pages.
Heid et al., "Real time quantitative PCR," Genome Research, 6:986-994 [1996].
Heinzmann et al., "Genetic variants of IL-13 signalling and human asthma and atopy," Hum. Mol. Genet., 9:549-559 [2000].
Holland et al., "Detection of specific polymerase chain reaction product by utilizing the 5' → 3' exonuclease activity of *Thermus aquaticus* DNA polymerase," Proc. Natl. Acad. Sci., USA, 88:7276-7280 [1991].
Kricka, "Nonisotopic DNA Probing Techniques," Academic Press Inc., San Diego, CA [1992] title and copyright pages.
Kruse et al., "The polymorphisms S503P and Q576R in the interleukin-4 receptor α gene are associated with atopy and influence the signal transduction," Immunol., 96:365-371 [1991].
Livak et al., "Oligonucleotides with fluorescent dyes at opposite ends provide a quenched probe system useful for detecting PCR product and nucleic acid hybridization," PCR Methods and Applications, 4:357-362 [1995].
Melton et al., "Efficient *in vitro* synthesis of biologically active RNA and RNA hybridization probes from plasmids containing a bacteriophage SP6 promoter," Nucleic Acid Res., 12:7035-7056 [1984].
Milstein and Cuello, "Hybrid hybridomas and their use in immunohistochemistry," Nature, 305:537-40 [1983].
Mitsuyasu et al., "Ile50Val variant of IL4Rα upregulates IgE synthesis and associates with atopic asthma," Nature Genet., 19:119-120 [1998].
Mitsuyasu et al., "Cutting edge: dominant effect of Ile50Val variant of the human IL-4 receptor α-chain in IgE synthesis," J. Immunol., 162:1227-1231 [1999].
Sambrook et al., *Molecular Cloning: a Laboratory Manual*, 2nd ed., Cold Spring Harbor Laboratory Press [1989] title and copyright pages provided.
Schick et al., "Squamous cell carcinoma antigen 2 is a novel serpin that inhibits the chymotrypsin-like proteinases cathepsin G and mast cell chymase," J Biol. Chem., 272:1849-1855 [1997].
Schick et al., "Cross-class inhibition of the cysteine proteinases cathepsins K, L, and S by the serpin squamous cell carcinoma antigen 1: a kinetic analysis," Biochemistry, 37:5258-5266 [1998].
Schneider et al., "A serine proteinase inhibitor locus at 18q21.3 contains a tandem duplication of the human squamous cell carcinoma antigen gene," Proc. Natl. Acad. Sci. USA, 92:3147-3151 [1995].
Wang et al., "Effects of IL-4 and IL-13 on gene regulation and signal transduction of the primary human airway tissue cells," Abstract presented at the Joint Meeting of the CIS and AAI, entitled Immunology 2000, Seattle, WA May 12-16, 2000.
Wills-Karp et al., "Interleukin-13: Central Mediator of Allergic Asthma," Science, 282:2258-2261 [1998].

(Continued)

*Primary Examiner*—David Saunders
(74) *Attorney, Agent, or Firm*—Medlen & Carroll LLP (57) ABSTRACT

SCCA1 and SCCA2 genes, whose expression were greatly changed in a plurality of cells by stimulating respiratory tract epithelial cells with IL-4 or IL-13, were obtained as allergy related genes. Furthermore, elevation of blood level of expression products of these genes accompanying bronchial asthmatic attack was elucidated. This invention provides a method of testing for bronchial asthmatic attack that uses as indicators, expression levels of these genes in biological samples.

12 Claims, 4 Drawing Sheets

OTHER PUBLICATIONS

Yssel and Groux, "Characterization of T cell subpopulations involved in the pathogenesis of asthma and allergic disease," Int. Arch. Allergy Immunol., 121:10-18 [2000].

Zhu et al., "Pulmonary expression of interleukin-13 causes inflammation, mucus hypersecretion, subepithelial fibrosis, physiologic abnormalities, and eotaxin production," J. Clin. Invest., 103:779-788 [1999].

Izuhara, "A microarray-based approach to search for bronchial asthma-related genes," Allergology and Immunology, 8:1148-1152 [2001] Japanese publication and English translation.

Noguchi et al., "Haplotypes of the 5' region of the IL-4 gene and SNPs in the intergene sequence between and IL-4 and IL-13 genes are associated with atopic asthma," Hum. Immunol., 62:1251-1257 [2001].

Schick et al., "Cross-class inhibition of elastolytic cysteine proteinases by the human serpin SCCA1," Pediatric Research, 41:306A [1997].

Symula et al., "Functional screening of an asthma QTL in YAC transgenic mice," Nat. Genet., 23:241-244 [1999].

Izuhara, "Bronchial epithelial cells and Th2 type cytokine," English translation of an abstract presented at the 50th Annual Meeting of the Japanese Society of Allergology, Nov. 30-Dec. 2, 2000.

Kawashima et al., Squamous cell carcinoma-related antigen in children with atopic dermatitis, Pediatr. Int., 42:448-450 [2000].

Kuperman et al., "Direct effects of interleukin-13 on epithelial cells cause airway hyperreactivity and mucus overproduction in asthma," Nat. Med., 8:885-889 [2002].

Lee et al., "Interleukin-13 induces dramatically different transcriptional programs in three human airway cell types," Am. J. Cell Mol. Biol., 25:474-485 [2001].

Matsui et al., "Identificationof genes influenced by IL-4 and IL-13 in human bronchial epithelium and bronchial smooth muscle cells," English translation of an abstract presented at the 30th Annual Meeting of the Japanese Society for Immunology, Nov. 14-16, 2000.

Rivas et al., "Identification of aberrantly regulated genes in diseased skin using the cDNA differential display technique," J. Invest. Dermatol., 108:188-194 [1997].

Shepard, "Uses of expression microarrays in studies of pulmonary fibrosis, asthma, acute lung injury and emphysema," Chest, 121:21S-25S [2002].

Yuyama et al., "Identification of genes influenced by IL-4 or IL-13 in human bronchial epithelium and bronchial smooth muscle cells," English translation of an abstract presented at the 50th Annual Meeting of the Japanese Society of Allergology, Nov. 30-Dec. 2, 2000.

Yuyama et al., "The analysis of squamous cell carcinoma antigen (SCCA), whose expression is induced by IL-4 and IL-13 in human bronchial epithelial cells," English translation of an abstract presented at the 51th Annual Meeting of the Japanese Society of Allergology, Oct. 29-31, 2001.

Yuyama et al., "Analysis of novel disease-related genes in bronchial asthma," Abstract presented at the Keystone Symposium entitled Rethinking the Pathogenesis of Asthma, Santa Fe, NM, Feb. 8-13, 2002.

Yuyama et al., "Analysis of novel disease-related genes in bronchial asthma," *Cytokine*, 19:287-296, 2002.

Stenman et al., "Detection of squamous-cell carcinoma antigen-expressiong tumour cells in blood by reverse transcriptase-polymerase chain reaction in cancer of the uterine cervix," *Int J Cancer (Pred Oncol)*, 74:75-80, 1997.

\* cited by examiner

METHOD OF TESTING FOR BRONCHIAL ASTHMA

This Application claims priority under 35 U.S.C. § 119 to Japanese Patent Application Ser. No. 2001-239857, filed on Aug. 7, 2001.

FIELD OF THE INVENTION

The present invention relates to a method of testing for bronchial asthmatic attack.

BACKGROUND OF THE INVENTION

Bronchial asthma is considered to be a multifactorial disease. In other words, bronchial asthma is caused by the interaction of many different genes, each of which is influenced by various environmental factors. Thus, it has been extremely difficult to identify a specific gene which causes bronchial asthma.

Currently, bronchial asthma is categorized as a chronic inflammatory disease of the respiratory tract. It has been pointed out that allergic reactions at the respiratory tract mucosa and bronchial smooth muscle is closely involved in pathologic formation of bronchial asthma. Therefore, understanding the condition of allergic reactions in these tissues is an important issue in diagnosis of bronchial asthma. In addition, control of allergic reactions is an issue in treatment of bronchial asthma.

On the other hand, the expression of mutated or defective genes, or overexpression or reduction of the expression of specific gene is thought to be involved in allergic diseases. To elucidate the role of gene expression in diseases, it is necessary to understand how a gene is involved in triggering disease onset and how expression of the gene is altered by external stimulants such as drugs.

Incidentally, atopic diathesis that is accompanied by hyperproduction of IgE antibodies is seen in many bronchial asthma patients. Many causes are considered for bronchial asthma, but there is no doubt that atopic diathesis is a cause of hypersensitivity in many patients. It has been predicted that the mechanism of respiratory tract occlusion in asthmatic attack is contraction of the bronchial smooth muscle, or edema and respiratory tract endocrine enhancement of the respiratory tract mucosa. I-type allergic reaction in the respiratory tract due to exposure to pathogenic allergen has an important role in such changes in the respiratory tract.

In recent years, IL-4 and IL-13 have been suggested to have important roles in the onset of bronchial asthma. Therefore, for example, in the respiratory tract epithelial cells and bronchial smooth muscles, genes that change their expression level due to IL-4 and IL-13 are thought to be related to bronchial asthma. However, based on such concept, there have been no reports on isolation of genes that specifically change their expression level due to IL-4 and IL-13.

In recent diagnosis of allergic diseases, history taking, and confirmation of the patient's family history and own anamnesis are important factors in general. In addition, for diagnosis of allergy based on more objective information, a test method using patient's blood sample and method for observing patient's immune response to allergen are also performed. Examples of the former method are the allergen-specific IgE measurement, leukocyte histamine release test, lymphocyte stimulating test, or the like. Presence of an allergen-specific IgE is a proof for the allergic reaction to that allergen. However, in some patients, allergen-specific IgE may not necessarily be detected. Furthermore, the assay principle of IgE requires performing tests for all of the allergens necessary for diagnosis. Leukocyte histamine release test and lymphocyte stimulating test are the methods for observing the immune system reaction toward a specific allergen in vitro. These methods are complicate in operation.

On the other hand, another method is also known, wherein the immune response observed when a patient is actually contacted with an allergen is used for diagnosing an allergy (latter method). Such a test includes the prick test, scratch test, patch test, intradermal reaction, or induction test. Indeed these tests allow the direct diagnosis of patient's allergic reaction but they can be said to be highly invasive tests wherein patients are actually exposed to allergen.

In addition, regardless of the allergen types, test methods for proving the involvement of allergic reaction are also attempted. For example, a high serum IgE titer may indicate the occurrence of allergic reaction in the patient. The serum IgE titer is information corresponding to the total amount of allergen-specific IgE. Though it is easy to determine the total amount of IgE regardless of the type of allergen, IgE titer may be reduced in some patients with a non-atopic bronchitis or the like.

Therefore, a marker (indicator) for an allergic disease that is not only less risky to patients but also capable of readily providing information necessary for diagnosis would be useful.

Particularly, bronchial asthmatic attack due to allergic reaction markedly inhibits patient's respiration, and, in severe cases, it may bring about death due to respiratory insufficiency. Therefore, prompt identification of the cause, and appropriate treatment must be given to patients affected with bronchial asthmatic attack. However, there are no reports on genes found to have a relation to bronchial asthmatic attack.

Regardless of the presence or absence of an attack, there are many reports on attempts to isolate genes relating to patients with allergic diseases. Genes that can be isolated by such an approach can be said to be genes relating to allergic diathesis. In contrast, genes relating to the attack can be expected to be useful as an indicator for diagnosis of the attack and for treatment of attacks needing greatly urgent clinical treatment.

SUMMARY OF THE INVENTION

An objective of the present invention is to provide an indicator enabling the test for bronchial asthmatic attack, in particular. Another objective of the invention is to provide a method of testing for bronchial asthmatic attack based on the indicator.

Deep involvement of IL-4 and IL-13 in allergic reaction has been suggested by several reports. For example, in an IL-4 knockout mouse (Yssel, H and Groux, H: Int. Arch. Allergy Immunol., 121; 10–18, 2000) and in a STAT6 knockout mouse (Akimoto, T. et al.: J. Exp. Med., 187, 1537–1542, 1998), respiratory tract hypersensitivity disappears. In a mouse model, IL-13 is involved in forming asthma-like pathology regardless of IgE production and Th2 type (Wills-Karp, M. et al.: Science, 282, 2258–2261, 1998; Grunig, G. et al.: Science, 282, 2261–2263, 1998; Zhu, Z. et al.: J. Clin. Invest., 103, 779–788, 1999).

Additionally, IL-4 receptors and IL-13 receptors are highly expressed in human respiratory tract epithelial cells and bronchial smooth muscles (Heinzmann, A. et al.: Hum. Mol. Genet., 9: 549–559, 2000). Accordingly, these tissues are thought to be target cells of IL-4 and IL-13. On the other hand, SNP present in IL-4 receptor α and IL-13 were shown to be one of the genetic causes of allergic diseases (Mitsuyasu, H., et al.: Nature Genet., 19, 119–120, 1998; Mitsuyasu, H., et al.: J. Immunol., 162: 1227–1231, 1999; Kruse, S., et al.: Immnol., 96, 365–371, 1999; Heinzmann, A. et al.: Hum. Mol. Genet., 9: 549–559, 2000). Furthermore, inhibition of IL-4 or IL-13 function by soluble IL-4 receptor α was shown to be effective as treatment for bronchial asthma (Borish, L. C. et al.: Am. J. Respir. Crit. Care Med., 160: 912–922, 1999).

According to the above, a strong relationship to allergic reactions, mainly respiratory symptoms in particular, has been suggested for IL-4 and IL-13. That is, genes constituting signal transduction pathway due to IL-4 and IL-13 may be genes that are closely related to allergic reactions.

Based on such line of thought, the inventors thought that, if genes indicating changes in expression levels were searched for when human bronchial epithelial cells were treated with IL-4 and IL-13, genes relating to allergic reactions could be isolated. There is a report that attempted, using a similar approach, to isolate genes whose expression level changed by IL-4 and IL-13 treatment (Wang et al., Immunology 2000, Seattle, May 12–16, 2000). However, since in known searching methods, the number of lots of cells used for analysis is small, and the range of changes in expression levels are not clear, specificity towards stimulation from IL-4 and IL-13 cannot be expected.

Therefore, to isolate genes that respond with higher specificity towards IL-4 and IL-13 stimulation, the inventors increased the number of lots of cells that become the object of analysis, and furthermore, selected those in which the change in expression level reached twice as much or more. Next, in the respiratory tract epithelial cells stimulated with IL-4 and IL-13, significant elevation of expression level of genes selected this way was confirmed.

Next, to confirm the relationship of selected genes to bronchial asthma, levels of each gene in the serum of bronchial asthma patients under various conditions were measured. As a result, specific genes were found to show significantly high values in the serum of bronchial asthma patients who have had attacks. Based on such findings as mentioned above, the inventors elucidated the existence of SCCA1 and SCCA2 genes having close relationship to bronchial asthmatic attacks.

Based on the above findings, the inventors found that tests for bronchial asthmatic attacks become possible by using these genes and proteins encoded by these genes as indicators, and completed this invention.

That is, this invention relates to a testing method described below, and its reagents.

(1) A method of testing for bronchial asthmatic attack using SCCA1 and/or SCCA2 as an indicator gene, said method comprising the steps of:
  (a) measuring the expression level of the indicator gene in a biological sample from a subject, and
  (b) comparing the expression level measured in (a) with that in a biological sample from a living body not affected by bronchial asthma.
(2) The method of (1), wherein the biological sample is blood.
(3) The method of (1), wherein the expression level of the gene is measured by PCR of the cDNA for the gene.
(4) The method of (1), wherein the expression level of the gene is measured by detecting a protein encoded by the gene.
(5) A reagent for testing for bronchial asthmatic attack, said reagent comprising an oligonucleotide that is at least 15 nucleotides long and that has a nucleotide sequence complementary to a polynucleotide having a nucleotide sequence of the SCCA1 and/or SCCA2 gene or to a complementary strand thereof.
(6) A reagent for testing for bronchial asthmatic attack, said reagent comprising an antibody recognizing a peptide having an amino acid sequence of SCCA1 and/or SCCA2 protein.

Incidentally, the existence of both SCCA1 and SCCA2 genes have been elucidated. Both SCCA1 and SCCA2 have been reported as genes encoding squamous cell carcinoma antigens, and are 45 kD genes belonging to the OVA family. They show 98% homology in the nucleotide sequences in the exon and show 92% homology at the amino acid level. The differences in the two nucleotide sequences can be discerned by PCR, and such. In the genome, both genes are mapped in 18q21.3 (Schneider, S. S. et al., Proc. Natl. Acad. Sci. USA, 92, 3147–3151, 1995). SCCA1 and SCCA2 have so far indicated the following utility.

SCCA1; squamous cell carcinoma antigen 1 (cysteine protease inhibitor):
  used as a diagnosis marker for squamous cell carcinoma (DE4139418-A).
SCCA2; squamous cell carcinoma antigen 2 (serine protease inhibitor):
  besides diagnosis marker, it is applied to the regulation of cell growth and apoptosis, or its agonist is applied to the treatment of cancer or psoriasis (WO9714425-A1).

Furthermore, it has been elucidated that, in response to IL-4 and IL-13, expression of both genes is enhanced in the respiratory tract epithelial cells (Wang et al., Immunology 2000, Seattle, May 12–16, 2000). However, it has been unknown that the blood level of the protein encoded by these genes is significantly elevated with bronchial asthmatic attack.

BRIEF DESCRIPTION OF THE DRAWINGS

FIG. 1 is a set of graphs indicating the result of measuring the expression level (copy/5 ng RNA) of SCCA1 gene in cultivated bronchial epithelial cells stimulated with IL-4 and IL-13, or with other cytokines. The top left is a graph indicating changes in expression level with time, 0, 6, 12, 24, and 48 hours after treatment. The numbers on the abscissa show the cultivation time. The top right is a graph indicating the change in expression level 24 hours after treatment with other cytokines. The bottom left is a graph indicating the expression level in each lot 24 hours after IL-4 and IL-13 stimulation. The bottom right is a graph indicating the changes in expression level 0, 24, 48, 72, and 96 hours after treating BEAS-2B cells with IL-4 and IL-13 stimulation. From left to right, each of the columns indicates actual measurement (raw data), β-actin scale factor (β-actin), and GAPDH scale factor (GAPDH).

DETAILED DESCRIPTION OF THE INVENTION

In this invention, bronchial asthmatic attack refers to a condition where respiratory tract stenosis occurs due to allergic reactions in the respiratory tract. More specifically, bronchial asthmatic attack is caused by contraction of the respiratory tract smooth muscles and by mucus in the bronchus and bronchiolar air cavity. Such changes in the respiratory tract are thought to be induced by smooth muscle contraction effect and vasostimulant effect of histamine, leukotriene, or prostaglandin, and such.

The method of testing for bronchial asthmatic attack of this invention includes the steps of measuring the expression level of SCCA1 and/or SCCA2 genes in a biological sample from a subject, and comparing the measured value with that for a living body not affected by bronchial asthma. As a result of comparing the two, when expression is enhanced compared to the living body not affected by bronchial asthma, the subject is judged to be in a condition of being affected with bronchial asthmatic attack. In this invention, a living body not affected by bronchial asthma includes healthy subjects and living body that is not exactly healthy but that has condition clearly diagnosed not as bronchial asthma.

In this invention, SCCA1 and SCCA2 genes together, which can be indicators of bronchial asthmatic attack, are referred to as indicator genes. In this invention, SCCA1 and SCCA2 include not only human's but also homologues of other species. Therefore, indicator genes in species other than humans, unless otherwise stated, refer to homologues of SCCA1 and SCCA2 genes intrinsic to those species, or either one of exogenous SCCA1 gene or SCCA2 gene that has been transformed into that individual.

In the blood of patients affected with bronchial asthmatic attack, the measured value of the indicator protein of this invention showed a significant increase. Therefore, testing of bronchial asthmatic attack can be performed using the expression level of indicator genes as an indicator.

In this invention, the expression level of indicator genes includes transcription of these genes to mRNA, and translation into proteins. Therefore, the method of testing for bronchial asthmatic attack of this invention is performed based on the expressivity of mRNA corresponding to the aforementioned genes, or on the comparison of expression level of proteins encoded by the aforementioned genes.

Usually, to compare the expression levels, a standard value is set based on, for example, the expression level of the aforementioned indicator genes in healthy subjects. Based on this standard value, the range of ±2 S. D. for example, is set as the permitted limit. The technique of setting standard values and permitted limits based on the measured value of indicator genes is well known. If the expression level of indicator genes in a subject is higher than the permitted limit, that subject is predicted to be affected with bronchial asthmatic attack. Additionally, if the expression level is within the permitted limit, or exceeds the permitted limit, the possibility of having had a bronchial asthmatic attack is predicted to be low.

Measurement of the expression level of an indicator gene in a test for bronchial asthmatic attack in the present invention can be performed according to the known gene analytical method. More specifically, for example, a hybridization technique with a nucleic acid as a probe that hybridizes to this gene, a gene amplification technique with a DNA hybridizing to the gene of this invention as a primer, or the like can be utilized.

The probe or primer used in the test of the present invention can be designed based on the nucleotide sequence of the indicator gene. The nucleotide sequence of the indicator gene is known. Genbank accession No. corresponding to the nucleotide sequence of each indicator gene is shown in Examples.

Genes of higher animals are generally accompanied by polymorphism in a high frequency. There exist many molecules that produce isoforms comprising different amino acid sequences from each other during the splicing process. Any genes associated with allergy which have a similar activity to that of the indicator gene are included in the indicator gene of the present invention, even though they carry mutation in the nucleotide sequence due to polymorphism and isoform.

As a primer or probe can be used a polynucleotide comprising the nucleotide sequence of the indicator gene or at least 15 nucleotides that are complementary to the complementary strand thereof. Herein, the term "complementary strand" means one strand of a double stranded DNA composed of A:T (U for RNA) and G:C base pairs to the other strand. In addition, "complementary" means not only those completely complementary to a region of at least 15 continuous nucleotides, but also having a homology of at least 70%, preferably at least 80%, more preferably 90%, and even more preferably 95% or higher. The degree of homology between nucleotide sequences can be determined by the algorithm, BLAST, etc.

Such polynucleotides are useful as the probe to detect an indicator gene, or as the primer to amplify the indicator gene. When used as a primer, those polynucleotides comprises usually 15 bp~100 bp, preferably 15 bp~35 bp of nucleotides. When used as a probe, DNAs comprising the whole sequence of the indicator gene (or a complementary strand thereof), or a partial sequence thereof that contains at least 15-bp nucleotides. When used as a primer, the 3' region thereof must be complementary to the indicator gene, while the 5' region can be linked to a restriction enzyme-recognition sequence or tag.

"Polynucleotides" in the present invention may be either DNA or RNA. These polynucleotides may be either synthetic or naturally-occurring. Also, DNA used as a probe for hybridization is usually labeled. Examples of labeling methods are those as described below. Herein, the term "oligonucleotide" means a polynucleotide with relatively low degree of polymerization. Oligonucleotides are included in polynucleotides. The labeling methods are as follows:

nick translation labeling using DNA polymerase I;

end labeling using polynucleotide kinase;

fill-in end labeling using Klenow fragment (Berger, S L, Kimmel, A R. (1987) Guide to Molecular Cloning Techniques, Method in Enzymology, Academic Press; Hames, B D, Higgins, S J (1985) Genes Probes: A Practical Approach. IRL Press; Sambrook, J, Fritsch, E F, Maniatis, T. (1989) Molecular Cloning: a Laboratory Manual, 2nd Edn. Cold Spring Harbor Laboratory Press);

transcription labeling using RNA polymerase (Melton, D A, Krieg, P A, Rebagkiati, M R, Maniatis, T, Zinn, K, Green, M R. (1984) Nucleic Acid Res., 12, 7035–7056); and non-isotopic labeling of DNA by incorporating modified nucleotides (Kricka, L J. (1992) Nonisotopic DNA Probing Techniques. Academic Press).

For testing for bronchial asthmatic attack using hybridization techniques, for example, Northern hybridization, dot blot hybridization, or DNA microarray technique may be used. Furthermore, gene amplification techniques, such as RT-PCR method may be used. By using the PCR amplification monitoring method during the gene amplification step in RT-PCR, one can achieve more quantitative analysis for the gene expression of the present invention.

In the PCR gene amplification monitoring method, the detection target (DNA or reverse transcript of RNA) is hybridized to probes that are dual-labeled at both ends with different fluorescent dyes whose fluorescences cancel each other out. When the PCR proceeds and Taq polymerase degrades the probe with its 5'-3' exonuclease activity, the two fluorescent dyes become distant from each other and the fluorescence becomes to be detected. The fluorescence is detected in real time. By simultaneously measuring a standard sample in which the copy number of the target is known, it is possible to determine the copy number of the target in the subject sample with the cycle number where PCR amplification is linear (Holland, P. M. et al., 1991, Proc. Natl. Acad. Sci. USA 88: 7276–7280; Livak, K. J. et al., 1995, PCR Methods and Applications 4 (6): 357–362; Heid, C. A. et al., 1996, Genome Research 6: 986–994; Gibson, E. M. U. et al., 1996, Genome Research 6: 995–1001). For the PCR amplification monitoring method, for example, ABI PRISM7700 (PE Biosystems) may be used.

The method of testing for bronchial asthmatic attack in the present invention can be also carried out by detecting a protein encoded by the indicator gene. Hereinafter, a protein encoded by the indicator gene is described as an indicator protein. For such test methods, for example, Western blotting method, immunoprecipitation method, and ELISA method may be employed using antibody that binds to the indicator protein.

Antibodies that bind to the indicator protein used in the detection may be produced by techniques known to those skilled in the art. Antibodies used in the present invention may be polyclonal or monoclonal antibodies (Milstein, C. et al., 1983, Nature 305 (5934): 537–40). For example, polyclonal antibody against an indicator protein may be produced by collecting the blood from mammals sensitized with the antigen, and separating the serum from this blood using known methods. As a polyclonal antibody, the serum containing polyclonal antibody as such may be used. As the occasion demands, a fraction containing polyclonal antibody can be further isolated from this serum. Also, monoclonal antibody may be obtained by isolating immune cells from mammals sensitized wIth the antigen, fusing these cells with myeloma cells, and such, cloning hybridomas thus obtained, and collecting the antibody as a monoclonal antibody from the culture of the hybridomas.

For detecting an indicator protein, these antibodies may be appropriately labeled. Alternatively, instead of labeling the antibody, a substance that specifically binds to the antibody, for example, protein A or protein G, may be labeled to arrange an indirect detection of indicator protein. More specifically, one example of an indirect detection method is ELISA.

Protein or its partial peptide used as an antigen may be obtained, for example, by inserting the gene or its portion into an expression vector, introducing it into an appropriate host cell to produce a transformant, culturing the transformant to express the recombinant protein, and purifying the expressed recombinant protein from the culture or the culture supernatant. Alternatively, amino acid sequences encoded by these genes, or oligopeptides comprising portions of the amino acid sequence encoded by the full-length cDNA are chemically synthesized to be used as the antigen.

In the method of testing for bronchial asthmatic attack based on this invention, the indicator genes that become the object of expression level and activity measurements are SCCA1 and/or SCCA2. SCCA1 and SCCA2 have very similar structures, and it is difficult to differentiate the two immunologically. For example, a kit to measure SCCA proteins immunologically is commercially available; however, the measured value of SCCA obtained using this kit is the sum of SCCA1 and SCCA2 values. That is, at present, measurements differentiating the two are not possible with the commercially available kit.

However, the expression level of both of the indicator genes of this invention were found to rise accompanying bronchial asthmatic attack. Therefore, bronchial asthmatic attack can be tested by measuring the overall expression level of these indicator genes.

Incidentally, monoclonal antibodies capable of differentiating the two have been reported, therefore, it is possible to selectively measure the two by immunological techniques (Clin Chim Acta 2000 295 107–127).

Furthermore, in this invention, bronchial asthmatic attack can be tested not only by the expression level of indicator genes, but also by using the activity of indicator proteins in biological samples as an indicator. The activity of indicator proteins refers to biological activity equipped in each protein. Detection of activity of the aforementioned indicator proteins can be performed based on known methods. Methods for measuring the activity of SCCA1 and SCCA2 are well known.

First, in the case of SCCA1, its activity can be measured as cysteine protease inhibitor activity of cathepsin-K, L, or S (Biochemistry 1998 37 5258–5266). On the other hand, SCCA2 has serine protease inhibitor activity of cathepsin-G and chymase. Therefore, the activity of SCCA2 can be measured as inhibitor activity (J.B.C. 1997 272 1849–1855). Specifically, activity of these indicator proteins can be found out by adding SCCA1 or SCCA2 with substrates of various proteases, and by using enzyme activity suppression as an indicator.

In the testing method of this invention, normally, biological sample collected from a subject is used as sample. Blood sample is preferred as the biological sample. As blood samples, whole blood, or plasma and serum obtained from whole blood may be used. Additionally, as biological samples of this invention, expectoration, nasal mucous secretion, bronchoalveolar lavage fluid, pulmonary abrasion cells, and such may be used besides blood. Collection methods for these biological samples are well known.

When the biological sample is cells of respiratory tract epithelial cells and such, samples for immunological measurements of the aforementioned proteins can be made by preparing a lysate. Otherwise, samples for measuring mRNA corresponding to the aforementioned genes can be made by extracting mRNA from this lysate. For extraction of lysate and mRNA of the biological sample, it is useful to utilize a commercially available kit. Otherwise, biological samples in the liquid form such as blood, nasal mucous secretion, and bronchoalveolar lavage fluid can be made into samples for measurement of proteins and genes by diluting with buffer and such, as necessary.

The measured value of expression level of indicator genes in cells can be corrected by known methods. As a result of correction, change in gene expression level in cells can be compared. Based on the measured value of expression level of genes that are expressed in the respiratory tract epithelial cells and do not show large fluctuations in their expression level regardless of the condition of the cell (housekeeping genes), correction of the measured value is performed by correcting the measured value of expression level of the genes that are to be used as indicators in this invention.

Furthermore, the present invention provides a reagent for the testing method of this invention. That is, this invention relates to a reagent for testing for bronchial asthma, said reagent comprising an oligonucleotide that comprises a nucleotide sequence complementary to a polynucleotide containing the nucleotide sequence of the indicator gene or to the complementary strand thereof and that comprises at least 15 nucleotide. Alternatively, this invention relates to a reagent for testing for bronchial asthma, said reagent comprising an antibody that recognizes a peptide containing the amino acid sequence of the indicator protein. Oligonucleotides and antibodies composing the reagent of this invention may be appropriately labeled, or immobilized onto a suitable carrier according to the assay format. Further, the reagent of this invention may be combined with, as well as the oligonucleotides or antibodies as described above, additional elements necessary for the test or storage to form a kit. Additional elements that can be used for constituting a kit are shown below. These elements may be previously mixed as necessary, or added with preservatives and antiseptics:

buffer for diluting reagents and biological samples;
positive standard sample;
negative standard sample;
substrate for measuring labels;
reaction vessel; and
manual describing the assay protocol.

Tests of bronchial asthmatic attack in this invention include, for example, the following tests. Even for patients who, while indicating bronchial asthmatic symptoms, cannot be judged to have allergic diseases by general testing, one can easily judge, by performing the test based on this invention, that the patients are in a condition where bronchial asthmatic attack due to allergic reactions occurs.

More specifically, elevation of indicator gene expression in patients indicating asthmatic attack indicates high probability that the cause of that symptom is an allergic disease. Among bronchial asthmatic attacks, there are those caused by allergic reactions and others that are not. The treatment methods for the two are completely different, therefore, to diagnose by which cause the bronchial asthmatic symptoms are being manifested is an extremely important step in treatment. The testing method of this invention provides extremely important information in identifying the cause of bronchial asthma.

Otherwise, this invention enables testing to judge whether the bronchial asthmatic attack is improving or not. The indicator proteins of this invention showed significant elevation of the measured value in the blood of patients affected with bronchial asthmatic attack. In addition, the indicator genes of this invention are genes that increase their expression in respiratory tract epithelial cells stimulated with IL-4 or IL-13. Respiratory tract epithelial tissues are tissues that show remarkable lesions in bronchial asthma. Therefore, proteins that are expression products of genes with fluctuating expression in respiratory tract epithelial cells stimulated with IL-4 or IL-13, which are cytokines that strongly induce allergic reactions, and those in which their measured value fluctuates in the blood are useful for judgment of therapeutic effect. More specifically, elevation of the measured value of indicator proteins in patients diagnosed with bronchial asthmatic attack indicates strong possibility that the attack is aggravated.

Tests of this invention include tests for predicting the possibility that bronchial asthmatic attack may occur in a relatively short time after testing, or for finding out, after recovery from a respiratory disorder, whether the cause of that respiratory disorder was due to bronchial asthma. Prediction of the attack is important in securing safety for the subjects. Additionally, finding out the cause of respiratory disorders experienced previously by the subject becomes an important information in determining a therapeutic course for a patient.

This invention elucidated genes whose expression increases during bronchial asthmatic attack. Furthermore, SCCA1 and SCCA2 genes in which their relation to bronchial asthma has been found in this invention are genes that increase their expression level by 10- to 20-fold or more in multiple lots of cells by stimulation from either IL-4 or IL-13, which are allergy related cytokines, and are genes that are closely related to allergies. There is a strong possibility that genes having such characteristics are the essential cause of allergic symptoms in bronchial asthmatic attack. Therefore, the indicator genes provided by this invention become a useful indicator to know reliably whether the bronchial asthmatic attack was caused by allergic symptoms. By enabling reliable diagnosis of bronchial asthmatic attack caused by allergies, accurate treatment can be selected at an early stage.

IL-4 and IL-13 are important factors that enhance allergic reactions. Therefore, genes whose expression increases accompanying stimulation by these factors may accomplish important roles in pathologic formation of allergic symptoms. Furthermore, indicator proteins provided by this invention all showed clear elevation of their measured values in the blood of patients affected with bronchial asthmatic attack. Studies focusing on changes of gene expression level accompanying IL-4 or IL-13 stimulation are not novel. However, any genes provided by this invention are genes observed to show elevation of concentration in the blood of patients affected with bronchial asthmatic attack. Therefore, in contrast to known allergy related genes obtained by a similar approach, the indicator genes of this invention can be thought to be genes accomplishing important roles in bronchial asthmatic attack. These findings elucidated by the inventors provide evidence that the existence of indicator genes of this invention is indispensable to bronchial asthmatic attack.

The expression level of indicator genes provided by this invention can be easily known, regardless of the type of allergen. Therefore, the pathology of an allergic reaction can be understood overall.

Additionally, the method of testing for allergies of this invention has low invasiveness towards patients since analysis of expression level can be carried out using a biological sample as the sample. Furthermore, regarding gene expression analysis, highly sensitive measurements are possible using small amounts of samples. Year after year, high throughput methods and decrease in cost are progressing in gene analysis technology. Therefore, in the near future, the method of testing for allergies of this invention is expected to become an important bed-side diagnostic method. In this sense, diagnostic value of these pathology related genes is high.

Any patents, patent applications, and publications cited herein are incorporated by reference.

The present invention will be explained in detail below with reference to examples, but it is not to be construed as being limited thereto.

EXAMPLE 1

Selection of Candidate Genes Using DNA Microarray

1. Cultivation of Normal Human Bronchial Epithelial Cells, and IL-4 or IL-13 Stimulation Three lots of normal human bronchial epithelial cells available from Clonetics were purchased (8F1756, 8F1548, 8F1805). Cells ($5 \times 10^5$) contained in one vial were divided into three equal parts ($1.67 \times 10^5/75$ cm$^2$ flask) for no stimulation, IL-4 stimulation, and IL-13 stimulation, and these were cultivated for approximately 8 to 10 days in SABM media (Clonetics) with medium exchange. During this procedure, BPE (bovine pituitary extract), hydrocortisone, hEGF, epinephrine, transferrin, insulin, retinoic acid, BSA-FAF, triiodothyronine, GA-1000 (gentamicin/amphotericin-B) were added to the media according to the attached protocol.

Before cytokine stimulation, the cells were washed with PBS, and then placed into SABM without added factors. IL-4 (10 ng/mL) and IL-13 (50 ng/mL) (both from Peprotech) were added thereto, and this was cultivated for 24 hours. Observation of changes with passage of time (0, 6, 12, 24, and 48 hours) was carried out in a similar manner.

2. Other Cytokine Stimulation of Normal Human Bronchial Epithelial Cells

Using cells from lot 8F1548, cultivation was performed similarly to that of 1. In place of IL-4 and IL-13, 50 ng/mL of TNFα, IL-1β, IL-5, IL-6, and IL-9 (all from Peprotech) were added and cultivated for 24 hours.

3. Preparation of RNA for GeneChip

Respiratory tract epithelial cells treated as mentioned above were dissolved in Isogen (Nippon Gene; Wako Pure Chemicals), and from this solution, RNA was separated according to a protocol attached to Isogen. After addition of chloroform, this was agitated, then centrifuged, and its aqueous layer was collected. Next, isopropanol was added, this was agitated, and then centrifuged to collect the precipitated total RNA.

4. cDNA Synthesis for GeneChip

Single stranded cDNA was prepared from 5 μg of total RNA, which was prepared from cells of lot 8F1756, by reverse transcription using Superscript II Reverse Transcriptase (Life Technologies) following the method of Expression Analysis Technical Manual by Affymetrix, and by using T7-(dT)$_{24}$ (Amersham Pharmacia) as a primer. The T7-(dT)$_{24}$ primer comprises a nucleotide sequence in which d(T)$_{24}$ is added to a T7 promoter nucleotide sequence, as shown below. T7-(dT)$_{24}$ primer (SEQ ID NO: 1) 5'-GGCCAGTGAATTGTAATACGACTCACTATAGGGAGGCGG-(dT)$_{24}$-3'

Next, according to Expression Analysis Technical Manual, DNA ligase, DNA polymerase I, and RNase H were added to synthesize double stranded cDNA. After phenol-chloroform extraction of cDNA, this was passed through Phase Lock Gels, and was purified by ethanol precipitation.

Furthermore, using BioArray High Yield RNA Transcription Labeling Kit, biotin-labeled cRNA was synthesized. Using RNeasy Spin column (QIAGEN), cRNA was purified and then fragmented by treatment with heat.

To a hybridization cocktail, 12.5 μg of this cRNA was added according to Expression Analysis Technical Manual. This was placed into an array and was hybridized for 16 hours at 45° C.

After the array was washed, streptavidin phycoerythrin was added for staining. After washing, a mixed antibody solution of normal goat IgG and biotinylated goat IgG was added to the array. Furthermore, in order to enhance fluorescence intensity, streptavidin phycoerythrin was added again for staining. After washing, this was set into a scanner and was analyzed by a GeneChip software.

5. GeneChip Analysis

Data analysis was performed using Suite, which is a GeneChip analysis software. Average Intensity (1) and Background Average (2) were investigated by Absolute Analysis, and 3 average values obtained for no stimulation, IL-4 stimulation, and IL-13 stimulation by subtracting (2) from (1) were used as scale factors for comparison analysis.

First, absolute analysis was performed to analyze one chip data. Positives and negatives were determined by comparing the fluorescence intensity of perfect match and mismatch of a probe set. Judgment into three categories of Absolute Calls, which are P (present), A (absent), and M (marginal), were made by values of Pos Fraction, Log Avg, and Pos/Neg.

Pos Fraction; ratio of positive pairs.

Log Avg; average of the log of fluorescence intensity ratio between probe cells of perfect match and mismatch.

Pos/Neg; ratio of the number of positive pairs and negative pairs.

Additionally, Average Difference (Avg Diff), which is the average value of the difference in fluorescence intensities between probe cells of perfect match and mismatch, was calculated for each gene.

Next, Comparison Analysis was performed on two sets of data. Comparisons were made between no stimulation and IL-4 stimulation, or between no stimulation and IL-13 stimulation, and differences in expression levels were ranked as follows. Judgment into 5 categories of difference calls, which are I, D, MI, MD, and NC, were made from values of Inc/Dec, Inc Ratio, Dpos-Dneg Ratio, and Log Avg Ratio Change.

Inc: Number of probe pairs that corresponded to IL-4 stimulation or IL-13 stimulation and no stimulation and that were judged to show increased expression levels for IL-4 stimulation or IL-13 stimulation.

Dec: Number of pairs judged to show decreased expression levels for IL-4 stimulation or IL-13 stimulation.

Inc/Dec: Ratio of the number of pairs judged to be Inc and number of pairs judged to be Dec.

Inc Ratio: Number of pairs judged to be Inc/number of pairs actually used.

Dpos/Dneg Ratio: Ratio between the number of Neg Change subtracted from that of Pos Change, and the number of pairs actually used.

Pos Change: Difference between the number of positive pairs in Absolute Analysis of IL-4 simulation or IL-13 stimulation, and the number of positive pairs in Absolute Analysis of no stimulation.

Neg Change: Difference between the number of negative pairs in Absolute Analysis of IL-4 simulation or IL-13 stimulation, and the number of negative pairs in Absolute Analysis of no stimulation.

Log Avg Ratio Change: Difference between Log Avg in Absolute Analysis of IL-4 stimulation or IL-13 stimulation and no stimulation.

Increased: I,

Decreased: D,

Marginally Increased: MI,

Marginally Decreased: MD, and

No Change: NC

Additionally, S66896 and U19557 (both are GenBank Acc. No.) were selected as genes whose expression was enhanced due to IL-4 simulation or IL-13 stimulation by values of Fold Change, which is a ratio of Avg Diff in Absolute Analysis of no stimulation with IL-4 simulation or no stimulation with IL-13 stimulation. S66896 probe corresponds to SCCA1 gene, and U19557 to SCCA2. Table 1 shows the value of Fold Change of S66896 and U19557 in respiratory tract epithelial cells by lot number.

TABLE 1

| Probe | Gene name | 8F1756 | 8F1548 | 8F1805 |
|---|---|---|---|---|
| | | IL-4 | | |
| S66896 | SCCA1 | 22.5 | 11.1 | 14.5 |
| U19557 | SCCA2 | 21.7 | 25.6 | 19.4 |
| | | IL-13 | | |
| S66896 | SCCA1 | 17.4 | 14.1 | 7.1 |
| U19557 | SCCA2 | 15.6 | 28.8 | 18.7 |

As evident from Table 1, SCCA1 and SCCA2 are genes that show 10- to 20-fold or greater expression level due to stimulation by either IL-4 or IL-13, which are allergy related cytokines, and are closely related to allergies. Furthermore, changes in the expression levels of these genes were commonly seen in different lots.

EXAMPLE 2

Confirmation of Expression Level of Candidate Genes

To quantitatively confirm the expression level of SCCA1 and SCCA2 genes selected in Example 1, cultivated respiratory tract epithelial cells (Clonetics) were used to further perform quantitative PCR by ABI 7700. Three lots, 8F1756, 8F1548, and 8F1805, were used for the cultivated cells. Primer and TaqMan probe used for measurements by ABI 7700 were designed by Primer Express (PE Biosystems) based on sequence information of each gene. The 5'-end of TaqMan probe is labeled with FAM (6-carboxy-fluorescein) and the 3'-end is labeled with TAMRA (6-carboxy-N,N,N', N'-tetramethylrhodamine). Nucleotide sequences of oligonucleotides used for forward primer (F), reverse primer (R), and TaqMan probe (TP) of each gene are as shown below. Genbank Accession No. corresponding to the nucleotide sequence of each indicator gene is shown in parenthesis following the name.

```
SCCA1 (s66896)
F:   agccgcggtctcgtgc            (SEQ ID NO:2)

R:   ggcagctgcagcttctg           (SEQ ID NO:3)

TP:  aaggcctttgtggaggttacagaggaggga  (SEQ ID NO:4)

SCCA2 (u19557)
F:   agccacggtctctcag            (SEQ ID NO:5)

R:   gcagctgcagcttcca            (SEQ ID NO:6)

TP:  aaggcctttgtggaggtcactgaggaggga  (SEQ ID NO:7)
```

Total RNA extracted by the aforementioned method was treated with DNase (Nippon Gene). Then, cDNA, which was reverse transcribed using random hexamer (GIBCO BRL) as primer, was used as a template. For a standard curve to calculate the number of copies, a plasmid clone containing a nucleotide sequence region that is amplified by both primers was prepared for each of the genes, and this was diluted stepwise to be used as template for carrying out the reaction. The composition of reaction solution for monitoring PCR amplification is shown in Table 2.

TABLE 2

| Composition of reaction in ABI-PRISM 7700 (Amount per well) | |
|---|---|
| Sterilized water | distilled 23.75 (μL) |
| 10x TaqMan buffer A | 5 |
| 25 mM MgCl$_2$ | 7 |
| dATP (10 mM) | 1.0 |
| dCTP (10 mM) | 1.0 |
| dGTP (10 mM) | 1.0 |
| dUTP (20 mM) | 1.0 |
| Forward Primer (10 μM) | 1.0 |
| Reverse Primer (10 μM) | 1.0 |
| TaqMan probe (2.0 μM) | 2.5 |
| AmpliTaq Gold (5 U/μL) | 0.25 |
| AmpErase UNG (1 U/μL) | 0.5 |
| Template solution | 5 |
| Total | 50 |

Additionally, to correct the differences of cDNA concentration in the sample, similar quantitative analysis was performed for β-actin gene and glyceraldehyde-3-phosphate dehydrogenase (GAPDH) gene as internal standards for correction. By correcting based on the number of copies of these genes, the number of copies of the genes of interest was calculated.

Figure 1:
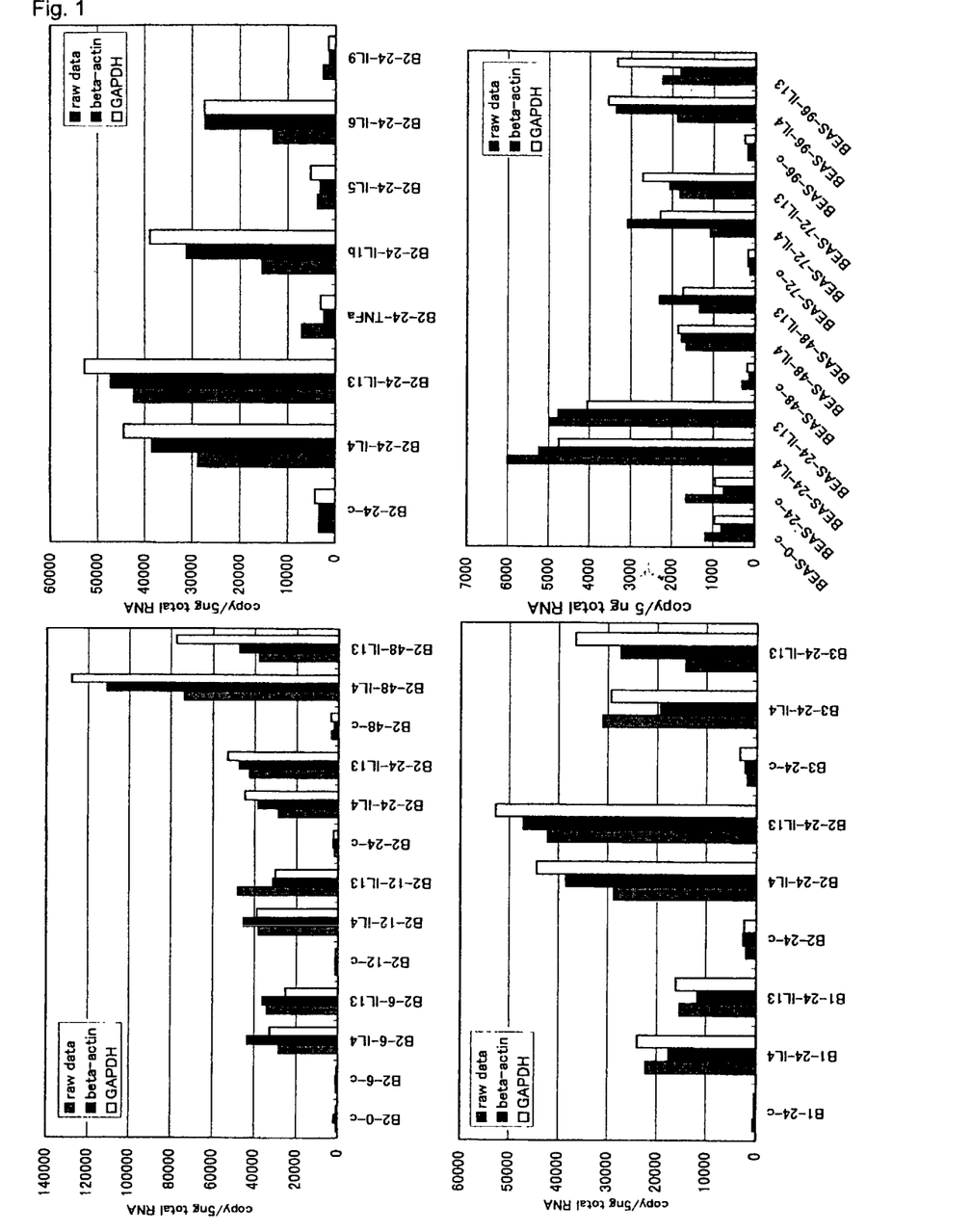
Figure 2:
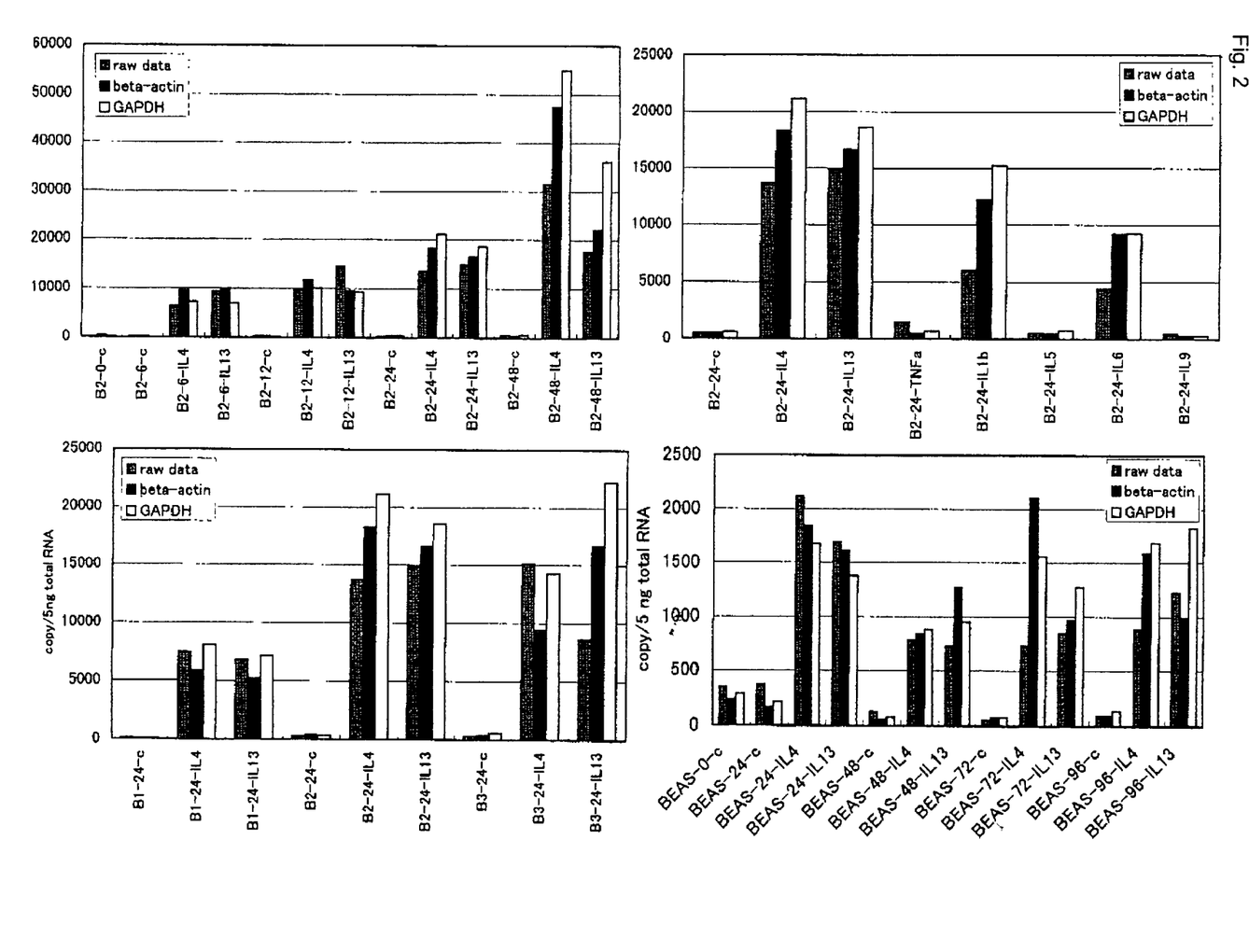
FIG. 2 is a set of graphs indicating the result of measuring the expression level of SCCA2 gene in cultivated bronchial epithelial cells simulated with IL-4 and IL-13, or with other cytokines. Each graph indicates analogous content to that of each graph in FIG. 1.

Primers and probes for measuring β-actin or GAPDH were those packaged with TaqMan β-actin Control Reagents (PE Biosystems). The nucleotide sequences are as shown below. The β-actin-corrected expression levels (copy/5 ng RNA) for each of the genes are shown in FIGS. 1 and 2.

Furthermore, the results of averaging fold change values from three lots when β-actin correction was performed and the unstimulated value was taken to be 1, are shown in Table 3.

TABLE 3

| Name of gene | IL-4 stimulation | IL-13 stimulation |
|---|---|---|
| SCCA1 | 30.3 ± 18.7 | 25.3 ± 10.3 |
| SCCA2 | 55.9 ± 23.0 | 56.6 ± 16.1 |

```
β-actin forward primer                  (SEQ ID NO:8)
        TCA CCC ACA CTG TGC CCA TCT ACG A β-actin reverse primer                  (SEQ ID NO:9)
        CAG CGG AAC CGC TCA TTG CCA ATG G β-actin TaqMan probe                    (SEQ ID NO:10)
        (FAM)ATGCCC-T(TAMRA)-CCCCCATGCCATCCTGCGTp-
        3'
GAPDH forward primer                    (SEQ ID NO:11)
        GAAGGTGAAGGTCGGAGT GAPDH reverse primer                    (SEQ ID NO:12)
        GAAGATGGTGATGGGATTTC GAPDH TaqMan probe                      (SEQ ID NO:13)
        (FAM)CAAGCTTCCCGTTCTCAGCC(TAMRA)-3'
```

-continued

FAM:    6-carboxy-fluorescein
TAMPA:  6-carboxy-N,N,N',N'-tetramethylrhodamine

As a result of quantitative PCR, the expression levels of both SCCA1 and SCCA2 genes in the respiratory tract epithelial cells, where both genes were selected in Example 1, were elevated by several tenfolds or more in three different respiratory tract epithelial cells due to IL-4 or IL-13 stimulation. Based on these results, elevation of expression levels of these indicator genes in response to IL-4 and IL-13 could be predicted in respiratory tract epithelial cells.

The indicator genes of this invention show common behavior among different lots of bronchial epithelial cells by IL-4 and IL-13 stimulation known to have close relationship to allergic reactions. Therefore, the indicator genes of this invention can be thought to be important genes regulating the progress of allergic reactions.

EXAMPLE 3

Analysis of Blood SCCA

To further confirm the relation of SCCA1 and SCCA2 genes, which were found to be related to allergic reactions in Examples 1 and 2, to bronchial asthmatic attack, blood levels of proteins encoded by these genes were measured in living bodies under various conditions.

Serum was separated from blood of bronchial asthma patients and non-asthma patients, or from the same bronchial asthma patient during attack and during absence of the attack. Using an SCCA measurement kit (IMx, Dainabot), blood level of SCCA protein containing both SCCA1 and SCCA2 was measured. SCCA measurement kit uses antibodies that react against both SCCA1 and SCCA2, therefore a total of these indicator proteins can be measured.

Figure 3:
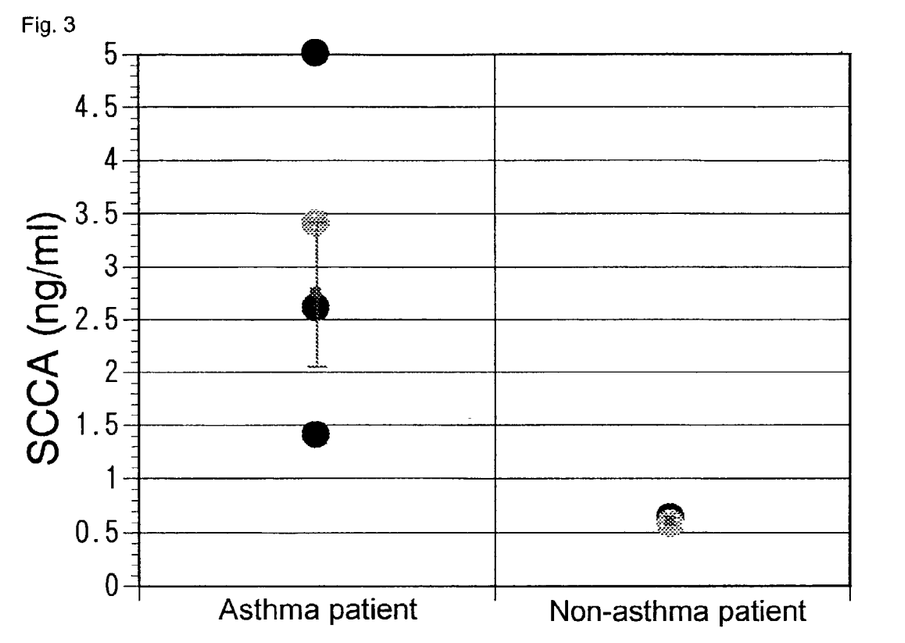
FIG. 3 is a graph indicating the measured value of serum SCCA in bronchial asthma patients and in non-asthma patients.
Figure 4:
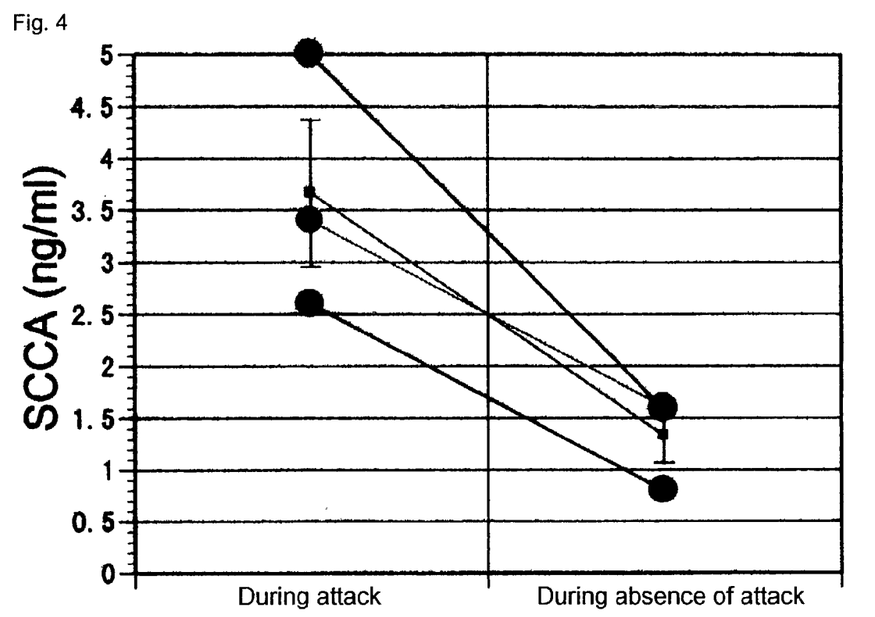
FIG. 4 is a graph indicating the measured value of serum SCCA in the same asthma patient during attack and during absence of an attack.

As a result, when bronchial asthma patients and non-asthma patients were compared, the blood SCCA level was significantly elevated in bronchial asthma patients (FIG. 3). Comparing the blood SCCA level in the same asthma patient during attack and during absence of an attack, the level was significantly elevated during attack (FIG. 4).

From these results, SCCA1 and SCCA2 were found to be genes related to allergies, and simultaneously, it was found that their blood levels significantly elevate during bronchial asthmatic attack compared to a healthy person or compared to a bronchial asthma patient during absence of the attack.

What is claimed is:

1. A method of testing for bronchial asthmatic attack, said method comprising the steps of:
   a) measuring the expression level of an indicator gene in a biological sample from a human subject having a symptom of a bronchial asthmatic attack, wherein said indicator gene is SCCA1, and
   b) comparing the expression level measured in step a), with that in a biological sample from a human living body not affected by bronchial asthma, wherein a higher level of SCCA1 in the biological sample from the subject indicates that the subject is having a bronchial asthma attack.

2. The method of claim 1, wherein the biological sample is blood.

3. The method of claim 1, wherein the expression level of the gene is measured by PCR of the cDNA for the gene.

4. The method of claim 1, wherein the expression level of the gene is measured by detecting a protein encoded by the gene.

5. A method of testing for bronchial asthmatic attack, said method comprising the steps of:
   a) measuring the expression level of an indicator gene in a biological sample from a human subject having a symptom of a bronchial asthmatic attack, wherein said indicator gene is SCCA2, and
   b) comparing the expression level measured in step a), with that in a biological sample from a human living body not affected by bronchial asthma, wherein a higher level of SCCA2 in the biological sample from the subject indicates that the subject is having a bronchial asthma attack.

6. The method of claim 5, wherein the biological sample is blood.

7. The method of claim 5, wherein the expression level of the gene is measured by PCR of the cDNA for the gene.

8. The method of claim 5, wherein the expression level of the gene is measured by detecting a protein encoded by the gene.

9. A method of testing for bronchial asthmatic attack, said method comprising the steps of:
   a) measuring the expression level of indicator genes in a biological sample from a human subject having a symptom of a bronchial asthmatic attack, wherein said indicator genes are SCCA1 and SCCA2, and
   b) comparing the expression level measured in step a), with that in a biological sample from a human living body not affected by bronchial asthma, wherein a higher level of SCCA1 and SCCA2, in the biological sample from the subject indicates that the subject is having a bronchial asthma attack.

10. The method of claim 9, wherein the biological sample is blood.

11. The method of claim 9, wherein the expression level of the genes is measured by PCR of the cDNA for the genes.

12. The method of claim 9, wherein the expression level of the genes is measured by detecting a protein encoded by the genes.

* * * * *

SEQUENCE LISTING

```
<160> NUMBER OF SEQ ID NOS: 13

<210> SEQ ID NO 1
<211> LENGTH: 63
<212> TYPE: DNA
<213> ORGANISM: Artificial Sequence
<220> FEATURE:
<223> OTHER INFORMATION: Synthetic

<400> SEQUENCE: 1
ggccagtgaa ttgtaatacg actcactata gggaggcggt tttttttttt tttttttttt    60
ttt                                                                  63

<210> SEQ ID NO 2
<211> LENGTH: 16
<212> TYPE: DNA
<213> ORGANISM: Artificial Sequence
<220> FEATURE:
<223> OTHER INFORMATION: Synthetic

<400> SEQUENCE: 2
agccgcggtc tcgtgc                                                    16

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
ggcagctgca gcttctg                                                   17

<210> SEQ ID NO 4
```

```
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Label FAM (6-carboxy-fluorescein)
<220> FEATURE:
<221> NAME/KEY: misc_binding
<222> LOCATION: (30)..(30)
<223> OTHER INFORMATION: Label TAMRA (6-carboxy-N,N,N',N'-
      tetramethylrhodamine)

<400> SEQUENCE: 4
aaggcctttg tggaggttac agaggaggga                                    30

<210> SEQ ID NO 5
<211> LENGTH: 16
<212> TYPE: DNA
<213> ORGANISM: Artificial Sequence
<220> FEATURE:
<223> OTHER INFORMATION: Synthetic

<400> SEQUENCE: 5
agccacggtc tctcag                                                   16

<210> SEQ ID NO 6
<211> LENGTH: 16
<212> TYPE: DNA
<213> ORGANISM: Artificial Sequence
<220> FEATURE:
<223> OTHER INFORMATION: Synthetic

<400> SEQUENCE: 6
gcagctgcag cttcca                                                   16

<210> SEQ ID NO 7
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Label FAM (6-carboxy-fluorescein)
<220> FEATURE:
<221> NAME/KEY: misc_binding
<222> LOCATION: (30)..(30)
<223> OTHER INFORMATION: Label TAMRA (6-carboxy-N,N,N',N'-
      tetramethylrhodamine)

<400> SEQUENCE: 7
aaggcctttg tggaggtcac tgaggaggga                                    30

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
tcacccacac tgtgcccatc tacga                                         25

<210> SEQ ID NO 9
<211> LENGTH: 25
```

```
<212> TYPE: DNA
<213> ORGANISM: Artificial Sequence
<220> FEATURE:
<223> OTHER INFORMATION: Synthetic

<400> SEQUENCE: 9
cagcggaacc gctcattgcc aatgg                                              25

<210> SEQ ID NO 10
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Label FAM (6-carboxy-fluorescein)
<220> FEATURE:
<221> NAME/KEY: misc_binding
<222> LOCATION: (7)..(7)
<223> OTHER INFORMATION: Label TAMRA (6-carboxy-N,N,N',N'-
      tetramethylrhodamine)

<400> SEQUENCE: 10
atgccctccc ccatgccatc ctgcgt                                             26

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
gaaggtgaag gtcggagt                                                      18

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
gaagatggtg atgggatttc                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Label FAM (6-carboxy-fluorescein)
<220> FEATURE:
<221> NAME/KEY: misc_binding
<222> LOCATION: (20)..(20)
<223> OTHER INFORMATION: Label TAMRA (6-carboxy-N,N,N',N'-
      tetramethylrhodamine)

<400> SEQUENCE: 13
caagcttccc gttctcagcc                                                    20
```